United States Patent
Terabe et al.

(10) Patent No.: US 12,343,079 B2
(45) Date of Patent: Jul. 1, 2025

(54) NON-TRANSITORY COMPUTER-READABLE STORAGE MEDIUM AND SUBJECTIVE OPTOMETRY SYSTEM

(71) Applicant: NIDEK CO., LTD., Aichi (JP)

(72) Inventors: Hirohisa Terabe, Aichi (JP); Taeko Horino, Aichi (JP)

(73) Assignee: NIDEK CO., LTD., Aichi (JP)

( * ) Notice: Subject to any disclaimer, the term of this patent is extended or adjusted under 35 U.S.C. 154(b) by 641 days.

(21) Appl. No.: 17/487,712

(22) Filed: Sep. 28, 2021

(65) Prior Publication Data

US 2022/0095908 A1      Mar. 31, 2022

(30) Foreign Application Priority Data

Sep. 29, 2020 (JP) .................. 2020-164173

(51) Int. Cl.
*A61B 3/00* (2006.01)
*A61B 3/032* (2006.01)

(52) U.S. Cl.
CPC ............ *A61B 3/0025* (2013.01); *A61B 3/032* (2013.01); *A61B 2560/0233* (2013.01)

(58) Field of Classification Search
CPC ... A61B 3/0025; A61B 3/0033; A61B 3/0041; A61B 3/0075; A61B 3/02; A61B 3/028; A61B 3/0285; A61B 3/032; A61B 3/103; A61B 2560/0233
See application file for complete search history.

(56) References Cited

U.S. PATENT DOCUMENTS

| | | |
|---|---|---|
| 5,867,248 A | 2/1999 | Hosoi et al. |
| 10,709,328 B2 | 7/2020 | Maier et al. |
| 2014/0129259 A1 | 5/2014 | Seriani |
| 2015/0160474 A1 | 6/2015 | Chang et al. |
| 2016/0098528 A1 | 4/2016 | Seriani |

(Continued)

FOREIGN PATENT DOCUMENTS

| | | |
|---|---|---|
| AU | 2013 341 741 | 5/2014 |
| JP | 2002-10978 A | 1/2002 |

(Continued)

OTHER PUBLICATIONS

Partial European Search Report dated Feb. 14, 2022, issued by the European Patent Office in counterpart European Patent Application No. 21199508.9.

(Continued)

*Primary Examiner* — Jack Dinh

(74) *Attorney, Agent, or Firm* — Sughrue Mion, PLLC

(57) ABSTRACT

A first information processing device acquires an instruction signal for instructing an operation of a subjective optometry device, and transmits a drive signal for causing the subjective optometry device to operate as instructed by the acquired instruction signal to the subjective optometry device. When the first information processing device is remote-accessed by a second information processing device, the first information processing device can acquire the instruction signal input to the second information processing device by a user via a network. The first information processing device can further acquire a response input by an examinee who visually recognizes a presented target, and can further generate an instruction signal instructing the operation of the subjective optometry device based on the acquired response.

3 Claims, 5 Drawing Sheets

(56) References Cited

U.S. PATENT DOCUMENTS

| | | |
|---|---|---|
| 2018/0064339 A1 | 3/2018 | Takii et al. |
| 2018/0301226 A1 | 10/2018 | Seriani |
| 2019/0148016 A1 | 5/2019 | Seriani |
| 2019/0148017 A1 | 5/2019 | Seriani |
| 2020/0243195 A1 | 7/2020 | Seriani |
| 2020/0272232 A1 | 8/2020 | Lussier et al. |
| 2020/0373016 A1 | 11/2020 | Seriani |
| 2021/0074430 A1 | 3/2021 | Seriani |
| 2021/0251482 A1 | 8/2021 | Seriani |
| 2021/0257099 A1 | 8/2021 | Seriani |

FOREIGN PATENT DOCUMENTS

| | | |
|---|---|---|
| JP | 2002-83156 A | 3/2002 |
| JP | 3660076 B2 | 6/2005 |
| JP | 2019-62978 A | 4/2019 |
| JP | 2020-18712 A | 2/2020 |
| KR | 10-2018-0027333 A | 3/2018 |

OTHER PUBLICATIONS

Communication issued on Jul. 23, 2024 by the Japanese Patent Office for Japanese Patent Application No. 2020-164173.

NON-TRANSITORY COMPUTER-READABLE STORAGE MEDIUM AND SUBJECTIVE OPTOMETRY SYSTEM

CROSS-REFERENCE TO RELATED APPLICATION

This application claims priority from Japanese Patent Application No. 2020-164173 filed on Sep. 29, 2020, the entire subject-matter of which is incorporated herein by reference.

TECHNICAL FIELD

The present disclosure relates to a non-transitory computer-readable storage medium storing an optometry control program executed in a subjective optometry system, and the subjective optometry system.

BACKGROUND

A subjective optometry device that measures optical characteristics such as an eye refractive power of a subject eye by arranging optical elements in front of an examinee and presenting an examination target on the subject eye through the optical elements, is known. For example, a subjective optometry device disclosed in JP-A-2020-018712 includes an eye refractive power measurement unit, a target presentation unit, and a controller. The eye refractive power measurement unit switches the optical elements to be arranged in an optometry window among a plurality of optical elements provided by the calibration optical system using a driver. The target presentation unit switches an examination target to be presented to the subject eye. The controller detects a user's operation on an operation panel and transmits a drive signal to the eye refractive power measurement unit and the target presentation unit based on the detected operation.

In the subjective optometry device in the related art, an examiner needs to be present at an examinee and to input a drive instruction for the next operation of the subjective optometry device based on a response from the examinee who visually recognizes the examination target. Therefore, in the subjective optometry device in the related art, it is difficult to smoothly execute the subjective optometry while reducing the burden on the examiner.

SUMMARY

A typical object of the present disclosure is to provide a non-transitory computer-readable storage medium storing an optometry control program and a subjective optometry system that can carry out a subjective optometry more smoothly.

A non-transitory computer-readable storage medium storing an optometry control program executed by a first information processing device in a subjective optometry system that includes a subjective optometry device having a calibration optical system that changes optical characteristics of a target light flux presented to a subject eye and is used for subjectively measuring optical characteristics of the subject eye, and the first information processing device connected to the subjective optometry device, the optometry control program including:
a drive control application program for realizing an application that transmits a drive signal for controlling an action of the subjective optometry device to the subjective optometry device; and
a self-optometry application program for realizing an application that automatically proceeds with an optometry based on a response input by an examinee,
in which the drive control application program includes instructions which, when the drive control application program is executed by a controller of the first information processing device, cause the first information processing device to perform:
an instruction signal acquisition step of acquiring an instruction signal for instructing an operation of the subjective optometry device; and
a drive signal transmission step of transmitting the drive signal for causing the subjective optometry device to operate as instructed by the acquired instruction signal to the subjective optometry device,
in which in a case where the first information processing device is remote-accessed by a second information processing device which is another information processing device connected via a network, the instruction signal input to the second information processing device by a user is acquired by the first information processing device via the network, in the instruction signal acquisition step, and
the self-optometry application program includes instructions which, when the self-optometry application program is executed by the controller of the first information processing device, cause the first information processing device to perform:
a response acquisition step of acquiring a response input by the examinee who visually recognizes a presented target; and
an instruction signal generation step of generating the instruction signal for instructing an operation of the subjective optometry device based on the acquired response.

A non-transitory computer-readable storage medium storing an optometry control program executed by a first information processing device in a subjective optometry system that includes a subjective optometry device having a calibration optical system that changes optical characteristics of a target light flux presented to a subject eye and a driver that drives the calibration optical system, and is used for subjectively measuring optical characteristics of the subject eye, and the first information processing device connected to the subjective optometry device, the optometry control program including:
a drive control application program for realizing an application that transmits a drive signal for controlling an action of the subjective optometry device to the subjective optometry device,
in which the drive control application program includes instructions which, when the drive control application program is executed by a controller of the first information processing device, cause the first information processing device to perform:
an instruction signal acquisition step of acquiring an instruction signal for instructing an operation of the subjective optometry device; and
a drive signal transmission step of transmitting the drive signal for causing the subjective optometry device to operate as instructed by the acquired instruction signal to the driver via a relay unit that converts the drive signal into a drive signal that enables to control the driver, in which in a case where the first information processing device is remote-accessed by a second information processing device which is another information processing device connected via a network, the instruction signal input to the second information processing device by a user is acquired by the first information processing device via the network, in the instruction signal acquisition step.

A subjective optometry system including:

a subjective optometry device having a calibration optical system that changes optical characteristics of a target light flux presented on a subject eye and is used to subjectively measure optical characteristics of the subject eye; and a first information processing device connected to the subjective optometry device, in which the first information processing device includes a controller to realize:

a drive control application that transmits a drive signal that controls an action of the subjective optometry device to the subjective optometry device; and a self-optometry application that automatically proceeds with an optometry based on a response input by an examinee, in which the drive control application executes:

an instruction signal acquisition step of acquiring an instruction signal for instructing an operation of the subjective optometry device; and a drive signal transmission step of transmitting the drive signal for causing the subjective optometry device to operate as instructed by the acquired instruction signal to the subjective optometry device, in which in a case where the first information processing device is remote-accessed by a second information processing device which is another information processing device connected via a network, the instruction signal input to the second information processing device by a user is acquired by the first information processing device via the network, in the instruction signal acquisition step, and the self-optometry application executes:

a response acquisition step of acquiring a response input by the examinee who visually recognizes a presented target; and an instruction signal generation step of generating the instruction signal for instructing an operation of the subjective optometry device based on the acquired response.

According to the non-transitory computer-readable storage medium and the subjective optometry system in the present disclosure, the subjective optometry is carried out more smoothly.

DETAILED DESCRIPTION

Overview

Figure 1:
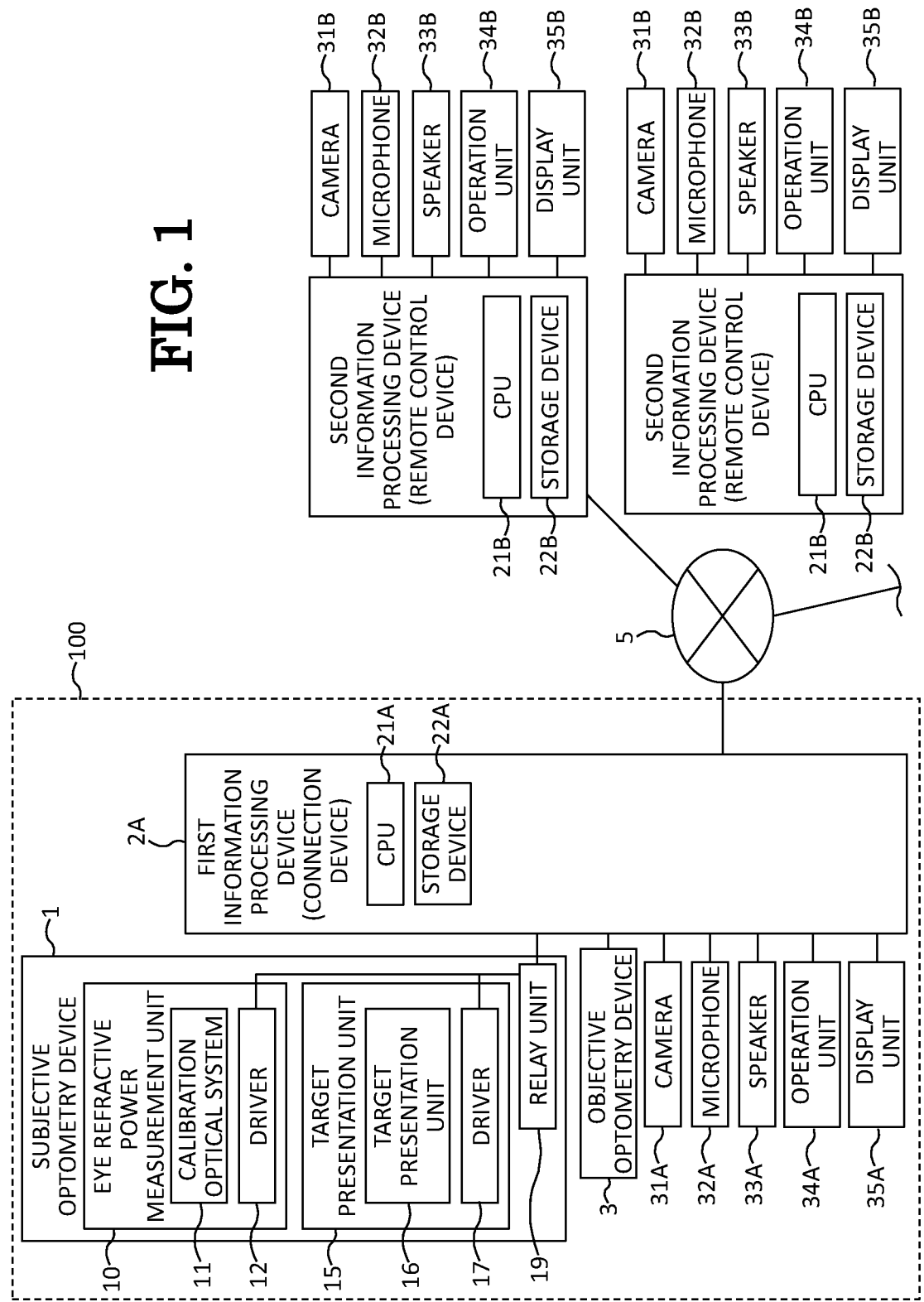
FIG. 1 is a block diagram showing a schematic configuration of a subjective optometry system 100.

The subjective optometry system exemplified in the present disclosure includes a subjective optometry device and a first information processing device. The subjective optometry device includes a calibration optical system that changes optical characteristics of a target light flux presented to the subject eye, and is used to subjectively measure the optical characteristics of the subject eye. The first information processing device is an information processing device that is connected to the subjective optometry device (hereinafter, sometimes the first information processing device may be referred to as a "connection device"). The optometry control program according to the present disclosure includes a drive control application program and a self-optometry application program. The drive control application program is a program for realizing an application (drive control application) that transmits a drive signal controlling an action of the subjective optometry device to the subjective optometry device. The self-optometry application program is a program for realizing an application (self-optometry application) that automatically proceed with the optometry based on a response input by the examinee.

By executing the drive control application program by a controller of the first information processing device, an instruction signal acquisition step and a drive signal transmission step are performed by the first information processing device. In the instruction signal acquisition step, the first information processing device acquires an instruction signal that instructs the operation of the subjective optometry device. In the drive signal transmission step, the first information processing device transmits the drive signal for causing the subjective optometry device to operate instructed by the acquired instruction signal to the subjective optometry device. The first information processing device can be remote-accessed by a second information processing device (hereinafter sometimes referred to as a "remote control device") which is another information processing device connected via the network. In this case, in the instruction signal acquisition step, the first information processing device can acquire the instruction signal input to the second information processing device by the user via the network.

By executing the self-optometry application program by the controller of the first information processing device, a response acquisition step and an instruction signal generation step are performed by the first information processing device. In the response acquisition step, the first information processing device acquires the response input by the examinee who visually recognizes the presented target. In the instruction signal generation step, the first information processing device generates an instruction signal that instructs the operation of the subjective optometry device based on the acquired response.

According to the technology exemplified in the present disclosure, when an instruction signal is input by a user (examiner) to a second information processing device that remote-accesses the first information processing device, the input instruction signal is acquired by the first information processing device. Subsequently, the drive signal for causing the subjective optometry device to carry out the instructed operation is transmitted from the first information processing device to the subjective optometry device. Therefore, the user can smoothly perform the optometry of the examinee from a remote place different from the location of the examinee. Furthermore, by executing the self-optometry application, the optometry of the examinee can be carried out appropriately even if the examiner does not proceed with the optometry. Therefore, the subjective optometry is appropriately carried out while the burden on the examiner is reduced.

Various devices can be used as the first information processing device (connection device) that executes the optometry control program, and the second information processing device (remote control device) that remote-accesses the first information processing device. For example, a personal computer (hereinafter, referred to as a "PC") may be used as at least one of the first information processing device and the second information processing device. In addition, a server, a mobile terminal, a smartphone, or the like may be used as at least one of the first information processing device and the second information processing device. The number of second information processing devices that can remote-access the first information processing device may be one or plural.

In addition, at least one of the first information processing device and the second information processing device may be configured by combining a plurality of devices. For example, the first information processing device may be configured with a device such as a personal computer and a dedicated controller including a controller and a storage device.

In addition, a storage device that stores the optometry control program can be selected as appropriate. For example, the optometry control program may be stored in the storage device built in the first information processing device or may be stored in a storage device that can be attached and detached to and from the first information processing device. The optometry control program may be stored in a storage device built in the dedicated controller described above. In addition, the optometry control program may be stored in a plurality of storage devices.

The first information processing device may further execute an optometry method switching step that switches a self-optometry which is an optometry carried out by the self-optometry application program and a remote optometry which is an optometry carried out in response to the instruction signal input to the second information processing device. In this case, each of the self-optometry and the remote optometry is appropriately carried out according to various situations and the like. For example, an appropriate optometry method can be selected from the self-optometry and the remote optometry according to the situation of facility or store where the subjective optometry device is installed, or the number of assigned personnel. In addition, an appropriate optometry method can also be selected according to the situation of the examinee. It is very convenient because it is not necessary to separately prepare a device for the self-optometry and a device for the remote optometry.

When the optometry for the examinee is started, the self-optometry may be carried out prior to the remote optometry in a state in which remote-access for one or a plurality of second information processing devices with respect to the first information processing device is established. In this case, since the self-optometry is started first, for the examinees to whom the self-optometry can be carried out, the optometry can be automatically carried out even if the examiner does not proceed with the optometry. In addition, in a case of the examinee to whom the self-optometry cannot be carried out, the optometry is switched to the remote optometry by the second information processing device for which the remote-access is established. Therefore, the optometry can be more smoothly carried out compared to a case of surely connecting the first information processing device and the second information processing device after the determination to switch from the self-optometry to the remote optometry.

In the optometry method switching step, when a situation of the self-optometry being carried out satisfies a predetermined condition, or when a switching instruction to switch to the remote optometry is input, the optometry may be switched to the remote optometry by at least one of the second information processing devices for which the remote-access is established. In this case, when a situation in which the self-optometry cannot be carried out on the examinee, switching from the self-optometry to the remote optometry can be appropriately carried out.

The conditions of a situation of the self-optometry when switching from the self-optometry to the remote optometry can be selected as appropriate. For example, when a predetermined time has elapsed without inputting the response from the examinee, the controller may determine that the condition for switching to the remote optometry is satisfied. In addition, when the response input by the examinee is inappropriate, the controller may determine that the condition for switching to the remote optometry is satisfied.

When the status of the self-optometry being carried out satisfies a predetermined condition, or when the switching instruction to switch to the remote optometry is input, the first information processing device may cause the second information processing device for which the remote-access is established, to perform a notification operation to the user. In this case, the user of the second information processing device can easily grasp that a situation occurred, in which the self-optometry cannot be carried out or the like. Therefore, switching from the self-optometry to the remote optometry can be carried out more smoothly.

It is also possible to change the method of switching the self-optometry and the remote optometry. For example, the first information processing device may appropriately switch the self-optometry and the remote optometry, according to the instructions input by the user (for example, the examiner).

At least one of an operation unit that outputs an operation signal by being operated by the user and a microphone that outputs an audio signal (hereinafter, simply referred to as an "operation unit/microphone") may be connected or mounted to the second information processing device. In an instruction signal input step, the instruction signal may be input by at least one of the operation signal and the audio signal. In this case, since the information processing device to which the operation unit/microphone is connected or mounted is used as the second information processing device, it is not necessary to configure the subjective optometry device such that the operation unit/microphone can be connected. As a result, the subjective optometry can be appropriately carried out in a state in which the configuration of the subjective optometry device is simplified.

At least one of general-purpose devices such as a keyboard, a mouse, and a touch panel may be used as the operation unit. In addition, a dedicated operation unit (for example, a joystick or the like) suitable for inputting the operation instructions in the subjective optometry may be used.

A camera may be connected to or mounted on the first information processing device. The first information processing device may further execute a display step of displaying a remote optometry screen to be visually recognized by the user who inputs an instruction signal to the second information processing device, on a display device. The remote optometry screen may include an area in which an operation image including information on the optical characteristics of the target light flux to be presented to the subject eye is displayed, and an area in which a captured image captured by the camera connected to or mounted on the first information processing device can be displayed. In this case, the user (examiner) of the second information processing device can check the captured image captured by the camera connected to the first information processing device (for example, the captured image of examinee) during remote optometry together with the operation image. Therefore, the remote optometry can be carried out more smoothly.

Another aspect of a subjective optometry system exemplified in the present disclosure includes a subjective optometry device and a first information processing device. The subjective optometry device includes a calibration optical system that changes the optical characteristics of the target light flux presented to the subject eye and a driver that drives the calibration optical system, and is used for measuring the optical characteristics of the subject eye subjectively. The first information processing device is the information processing device connected to the subjective optometry device. The optometry control program according to the present disclosure includes a drive control application program for realizing an application (drive control application) that transmits a drive signal for controlling the action of the subjective optometry device to the subjective optometry device. By executing the drive control application program by a controller of the first information processing device, an instruction signal acquisition step and a drive signal transmission step are performed by the first information processing device. In the instruction signal acquisition step, the first information processing device acquires an instruction signal that instructs the operation of the subjective optometry device. In the drive signal transmission step, the first information processing device transmits the drive signal for causing the subjective optometry device to operate instructed by the acquired instruction signal, to the driver via the relay unit. The relay unit converts the drive signal transmitted from the first information processing device into a drive signal that enables to control the driver. The first information processing device can be remote-accessed by a second information processing device which is another information processing device connected via the network. In this case, in the instruction signal acquisition step, the first information processing device acquires the instruction signal input to the second information processing device by the user, via the network.

In the subjective optometry device in the related art, sometimes a drive signal that controls the work of the driver is transmitted from a dedicated controller to the driver via a relay unit. The drive signal needs to be converted into a drive signal that enables to control the driver by the relay unit. In this case, as a method of using the subjective optometry device in the related art and the information processing device in combination, a method can be considered, in which the drive signal is transmitted from the controller to the driver via the relay unit by transmitting the control signal from the information processing device to the controller. However, since this method requires signal processing in the controller, problems such as operation delay of the driver may occur.

On the other hand, according to the technology exemplified in the present disclosure, the drive signal is transmitted from the first information processing device connected to the subjective optometry device to the driver via the relay unit. That is, the signal transmitted from the first information processing device does not need to go through the controller. Therefore, problems such as operation delay of the subjective optometry device are unlikely to occur. Furthermore, when the instruction signal is input by the user (examiner) to the second information processing device that remote-accesses the first information processing device, the input instruction signal is acquired by the first information processing device, and the drive signal to perform the instructed operation is transmitted from the first information processing device. Therefore, the user can smoothly perform the optometry of the examinee from a remote place different from the location of the examinee.

Embodiment (System Configuration)

Hereinafter, one of the typical embodiments in the present disclosure will be described with reference to the drawings. As shown in FIG. 1, a subjective optometry system 100 in the present embodiment includes a subjective optometry device 1 and a first information processing device 2A. The subjective optometry device 1 is used to subjectively measure the optical characteristics of the subject eye. The optical characteristics of the subject eye measured by the subjective optometry device 1 in the present embodiment is an eye refractive power. The measured eye refractive power may be at least one of a spherical power, a cylindrical power, an astigmatic axis angle, and the like of the subject eye. The first information processing device 2A is connected to the subjective optometry device 1. Hereinafter, the first information processing device 2A may be referred to as a connection device. In addition, the first information processing device 2A is remote-accessed by a second information processing device 2B which is another information processing device, via a network 5. Hereinafter, each device will be described in detail.

The subjective optometry device 1 will be described. The subjective optometry device 1 includes an eye refractive power measurement unit 10, a target presentation unit 15, and a relay unit 19.

The eye refractive power measurement unit 10 includes a calibration optical system 11 and a driver 12. The calibration optical system 11 changes the optical characteristics of the target light flux presented to the subject eye. That is, the calibration optical system 11 changes at least one of the spherical power, the cylindrical power, the astigmatic axis angle, polarization characteristics, and an amount of aberration of the target light flux. As an example, the calibration optical system 11 in the present embodiment changes the optical characteristics of the target light flux by switching the optical element arranged in an examination window in front of the subject eye among a plurality of optical elements. In the calibration optical system 11 in the present embodiment, a left eye lens disc and a right eye lens disc in which a plurality of optical elements are arranged on the same circumference are used. Each of the left eye lens disc and the right eye lens disc may be one or plural. As the optical element, for example, at least one of a spherical lens, a cylindrical lens, a cross cylinder lens, a rotary prism, a wave surface modulation element, and the like may be used. The driver 12 changes the optical characteristics of the target light flux by driving the calibration optical system 11. The driver 12 in the present embodiment drives the calibration optical system 11 by rotating each of the left eye lens disc and the right eye lens disc and then switching the optical element to be arranged in the examination window. For example, a step motor or the like can be used as the driver 12 The driver 12 is driven in response to the drive signal.

The target presentation unit 15 presents an examination target (for example, at least one of a Randold ring target, characters, and the like) on the subject eye, and switches the examination target to be presented to the subject eye. Specifically, the target presentation unit 15 includes a target presentation unit 16 and a driver 17. The target presentation unit 16 presents the examination target to the subject eye. For example, at least one of a space-saving type target projection device that projects the examination target onto the subject eye via a concave mirror, a chart projector that projects the examination target onto the screen, a display that displays the examination target, and the like can be adopted as the target presentation unit 16. The target presentation unit 16 is arranged at substantially the same height as the eye refractive power measurement unit 10 such that a distance from the subject eye is optically a predetermined distance. The driver 17 switches the examination target to be presented to the subject eye by driving the target presentation unit 16. The driver 17 is driven in response to the drive signal.

The relay unit 19 relays the drive signal between the first information processing device 2A and the drivers 12 and 17. In addition, in the present embodiment, a system of the drive signal output from the first information processing device 2A and a system of the drive signal that enables to control at least one of the drivers 12 and 17 are different from each other. The relay unit 19 in the present embodiment converts the drive signal received from the first information processing device 2A into a drive signal that enables to control the drivers 12 and 17, and transmits the drive signal to the drivers 12 and 17. Furthermore, as an example, when receiving one drive signal for driving two drivers 12 and 17 from the first information processing device 2A, the relay unit 19 in the present embodiment converts the received one drive signal into two drive signals for driving each of the two drivers 12 and 17, and transmits the two drive signals to each of the two drivers 12 and 17.

The first information processing device 2A and the second information processing device 2B will be described. At least any one of various information processing devices that can perform processing on various information can be adopted as the first information processing device 2A and the second information processing device 2B. As an example, a personal computer (hereinafter, referred to as a "PC") can be used as the first information processing device 2A and the second information processing device 2B in the present embodiment. However, the information processing device that can function as the first information processing device 2A and the second information processing device 2B in the present embodiment is not limited to the PC. For example, a server, a mobile terminal, a smartphone, or the like may be used as at least one of the first information processing device 2A and the second information processing device 2B. At least any one of the first information processing device 2A and the second information processing device 2B may be configured with a plurality of devices. For example, the first information processing device 2A may be configured with a dedicated controller including a controller and a storage device, and a personal computer.

The first information processing device 2A and the second information processing device 2B are connected to each other in a communicable state via a network (for example, the Internet) 5. In the example shown in FIG. 1, a case where a plurality of second information processing devices 2B are connected to one first information processing device 2A is illustrated. However, one second information processing device 2B may be connected to one first information processing device 2A. In addition, one second information processing device 2B may be connected to a plurality of first information processing devices 2A.

The first information processing device 2A is arranged at a base (for example, an optician, a hospital, or the like) where the subjective optometry for the examinee is carried out. The first information processing device 2A includes a CPU 21A and a storage device 22A. The CPU 21A is a controller that manages the control of the first information processing device 2A. The storage device 22A can store programs, various data, and the like. In the present embodiment, an optometry control program is stored in the storage device 22A.

The first information processing device 2A is connected to the subjective optometry device 1 (specifically, the relay unit 19 of the subjective optometry device 1) in a communicable state. As a connection standard between the first information processing device 2A and the subjective optometry device 1, various standards such as LAN can be adopted. In addition, the first information processing device 2A is connected to an objective optometry device 3 in a communicable state. The objective optometry device 3 objectively measures the optical characteristics of the subject eye (for example, at least one of the spherical power, the cylindrical power, and the astigmatic axis angle). As the connection standard between the first information processing device 2A and the objective optometry device 3, various standards such as LAN can be adopted. The objective optometry device 3 may be connected to the relay unit 19. A result of measurement by the objective optometry device 3 may be stored in the storage device included in the relay unit 19.

A camera 31A, a microphone 32A, a speaker 33A, an operation unit 34A, and a display unit 35A are connected to the first information processing device 2A. The camera 31A captures an image. In particular, the camera 31A in the present embodiment is used for capturing a moving image of the examinee. The microphone 32A converts sound into an audio signal to output. The speaker 33A converts the audio signal into sound. The operation unit 34A is operated by the user (for ex ample, examinee, and the like) for inputting various instructions. As the operation unit 34A, for example, at least one of a keyboard, a mouse, a touch panel, and the like may be used. In addition, as the operation unit 34A, a dedicated operation unit (for example, a joystick or the like) suitable for inputting the response of the subjective optometry may be used. The display unit 35A displays various images. Various devices capable of displaying images (for example, at least one of a monitor, a display, a projector, and the like) can be used as the display unit 35B.

The second information processing device 2B is arranged at a base of the examiner capable of advancing the optometry using the subjective optometry device 1. The second information processing device 2B includes a CPU 21B and a storage device 22B. The CPU 21B is a controller that manages the control of the second information processing device 2B. The storage device 22A can store programs, various data, and the like.

A camera 31A, a microphone 32A, a speaker 33A, an operation unit 34A, and a display unit 35A are connected to the second information processing device 2B. As these devices described above, various devices similar to the devices connected to the first information processing device 2A described above can be used.

(Application and Optometry Method)

The applications installed in the first information processing device 2A in the present embodiment will be described. As described above, an optometry control program for executing the optometry control processing (see FIG. 2) is stored in the storage device 22A included in the first information processing device 2A. The optometry control program includes a drive control application program for executing a drive control application and a self-optometry application program for executing a self-optometry application. The drive control application transmits a control signal for controlling the action of the subjective optometry device 1 to the subjective optometry device 1. The self-optometry application automatically progresses the optometry by the subjective optometry device 1 based on the response input by the examinee. The drive control application program for executing the drive control application and the self-optometry application program for executing the self-optometry application may be constructed and prepared separately, or may be incorporated into one program.

A subjective optometry method that can be performed by the subjective optometry system 100 in the present embodiment will be described. The subjective optometry system 100 in the present embodiment executes the self-optometry and the remote optometry. The self-optometry is an optometry carried out by the self-optometry application. That is, in the self-optometry, the optometry is automatically progressed based on the response input by examinee. The remote optometry is an optometry carried out in response to a signal (instruction signal) input to the second information processing device 2B. The second information processing device 2B can be arranged at a base different from the base where the subjective optometry device 1 is arranged. Therefore, according to the remote optometry, even if the base of the examiner and the base of the examinee are different from each other, the optometry proceeds smoothly by the examiner.

(Optometry Control Processing)

An example of optometry control processing carried out by the first information processing device 2A of the subjective optometry system 100 in the present embodiment will be described with reference to FIGS. 2 to 5. In the optometry control processing, for example, processing for controlling the self-optometry, processing for controlling the remote optometry, processing for switching between the self-optometry and the remote optometry, and the like are carried out. When the instruction to start the subjective optometry for the subject eye is input to the first information processing device 2A, the CPU 21A of the first information processing device 2A performs the optometry control processing shown in FIG. 2 according to the optometry control program.

First, the CPU 21A determines whether or not the remote access for one or a plurality of second information processing devices 2B to the first information processing device 2A is established when the optometry of the examinee is started (S1).

The "state in which the remote access is established" in the present embodiment indicates a state in which an instruction input to any of a plurality of information processing devices connected via the network 5 is transmitted to another information processing device via the network 5. For example, when remote access for the second information processing device 2B to the first information processing device 2A is established, the instruction input to the second information processing device 2B by the user is transmitted to the first information processing device 2A. As a result, the second information processing device 2B is in a state in which as if it is accessed to the first information processing device 2A at a different base.

Various methods can be used to make remote access for the second information processing device 2B to the first information processing device 2A be established. For example, by using a remote access service (RAS), the remote aces for the second information processing device 2B to the first information processing device 2A can be established. In this case, the second information processing device 2B is in a state of being accessed to applications other than the self-optometry application and the drive control application in the first information processing device 2A. In addition, by only the signals necessary for the first information processing device 2A to control the optometry control processing (refer to FIG. 2) being transmitted from the second information processing device 2B to the first information processing device 2A, the remote-access may be surely performed.

When the remote access for at least one second information processing device 2B to the first information processing device 2A is already established (YES in S1), the process proceeds to S3 as it is, and the self-optometry processing is performed. When any of the second information processing devices 2B does not remote-access the first information processing device 2A (NO in S1), the CPU 21A performs the self-optometry processing (S3) after making the remote access for at least one of the second information processing devices 2B be established (S2). That is, when the optometry for the examinee is started, the self-optometry processing (S3) is performed prior to the remote optometry processing (S6) in a state in which remote access for the second information processing device 2B to the first information processing device 2A is established. Therefore, for the examinees to whom the self-optometry can be carried out, the optometry can be automatically carried out even if the examiner does not proceed with the optometry. Furthermore, as will be described in detail later, for the examinees to whom the self-optometry cannot be carried out, the self-optometry is switched to the remote optometry by the second information processing device 2B for which the remote access is established. Therefore, the optometry can be carried out more smoothly compared to a case of making the first information processing device 2A and the second information processing device 2B be connected (remote-access is established) to each other after the determination to switch from the self-optometry to the remote optometry.

The self-optometry processing will be described with reference to FIG. 3. The processes of S11 to S18 in the self-optometry processing are performed by the self-optometry application. First, the CPU 21A acquires the objective optometry result (S11). As an example, the first information processing device 2A in the present embodiment acquires the objective optometry result for the same examinee from the objective optometry device 3 (refer to FIG. 1) connected via LAN or the relay unit 19. However, the CPU 21A may acquire the objective optometry result for the same examinee, for example, via a detachable memory, the network 5, or the like. In addition, the objective optometry result may be input by the user via the operation unit 34A or the like. If there is no objective optometry result for the same examinee, the process of S11 may be omitted.

The CPU 21A determines a content of the first examination in the self-optometry. The CPU 21A generates an instruction signal for instructing the subjective optometry device 1 to operate for executing the determined examination (S12). When the objective optometry result for the same examinee is acquired in S11, in S12, the content of the first examination (that is, the optical element to be firstly arranged in the examination window of the calibration optical system 11 and the type and size of the target to be presented in the target presentation unit 16) is determined according to the objective optometry result (for example, the eye refractive power (at least any one of the spherical power, the astigmatic power, and the astigmatic axis angle) measured for the same subject eye). As a result, the self-optometry processing is simplified. When the objective optometry result is not acquired in S11, in S12, the default content of examination may be determined as the content of the first examination.

Next, the CPU 21A acquires the instruction signal generated in S12 or S18 (described later), and transmits a drive signal for causing the subjective optometry device 1 to operate as instructed by the instruction signal to the subjective optometry device 1 (S13). As a result, in the subjective optometry device 1, the instructed operation is appropriately carried out. Specifically, in S13 in the present embodiment, at least one of the drive signal to the driver 12 for arranging the optical elements determined in S12 or S18 in the examination window of the calibration optical system 11 and the drive signal to the driver 17 for presenting the target determined in S12 or S18 in the target presentation unit 16 is transmitted to the subjective optometry device 1. When transmitting the drive signal to the subjective optometry device 1, the CPU 21A outputs a guidance voice according to the content of examination from the speaker 33A. Therefore, the examinee can see the presented examination target while appropriately understanding the content of examination.

In the present embodiment, the drive signal is transmitted from the first information processing device 2A to the drivers 12 and 17 via the relay unit 19 (refer to FIG. 1) described above. Therefore, the signal transmitted from the first information processing device 2A does not need to go through a dedicated controller or the like. Accordingly, since the signal processing by a dedicated controller and the like is omitted, the optometry is carried out more smoothly.

In the self-optometry, the examinee visually recognizes the examination target presented to the subject eye by the subjective optometry device 1 while understanding the content of examination by the guidance voice, and then, inputs a response of the visually recognized result to the first information processing device 2A. As an example, in the present embodiment, the response is input by operating the dedicated operation unit 34A suitable for inputting the response of the subjective optometry by the examinee. However, the response may be input by the general operation unit 34A. In addition, the response may be input by the audio signal converted by the microphone 32A.

The CPU 21A determines whether or not the response from the examinee is input (S15). When the response is input (YES in S15), the input response is stored in the storage device 22A (S16). Next, when a series of self-optometry is not completed yet (NO in S17), the CPU 21A determines the content of next examination based on the response from the examinee acquired in S15, and generates an instruction signal (S18).

As an example, in the present embodiment, when response from the examinee acquired in S15 is a correct response, the CPU 21A determines the content of next examination such that the target to be presented in the target presentation unit 16 becomes a target having a visual acuity value one step higher than that of the target displayed last time (for example, a target of which the size is one step smaller). In addition, when the response from the examinee acquired in S15 is an incorrect response, the CPU 21A determines the content of next examination such that the target to be presented in the target presentation unit 16 becomes a target having a visual acuity value one step lower than that of the target presented last time (for example, a target of which the size is one step larger). In addition, the CPU 21A determines the calibration degree of the optical element to be arranged in the examination window of the calibration optical system 11 as the content of next examination together with switching of the target. Next, the CPU 21A generates the instruction signal for instructing the subjective optometry device 1 to perform the next operation for executing the determined examination. That is, the instruction signal generated in S18 is at least any one of the instruction signal for arranging the determined optical element in the examination window of the calibration optical system 11, and the instruction signal for presenting the determined target in the target presentation unit 16. After that, the process returns to S13, and the drive signal is transmitted to the subjective optometry device 1 according to the instruction signal generated in S18.

Figure 2:
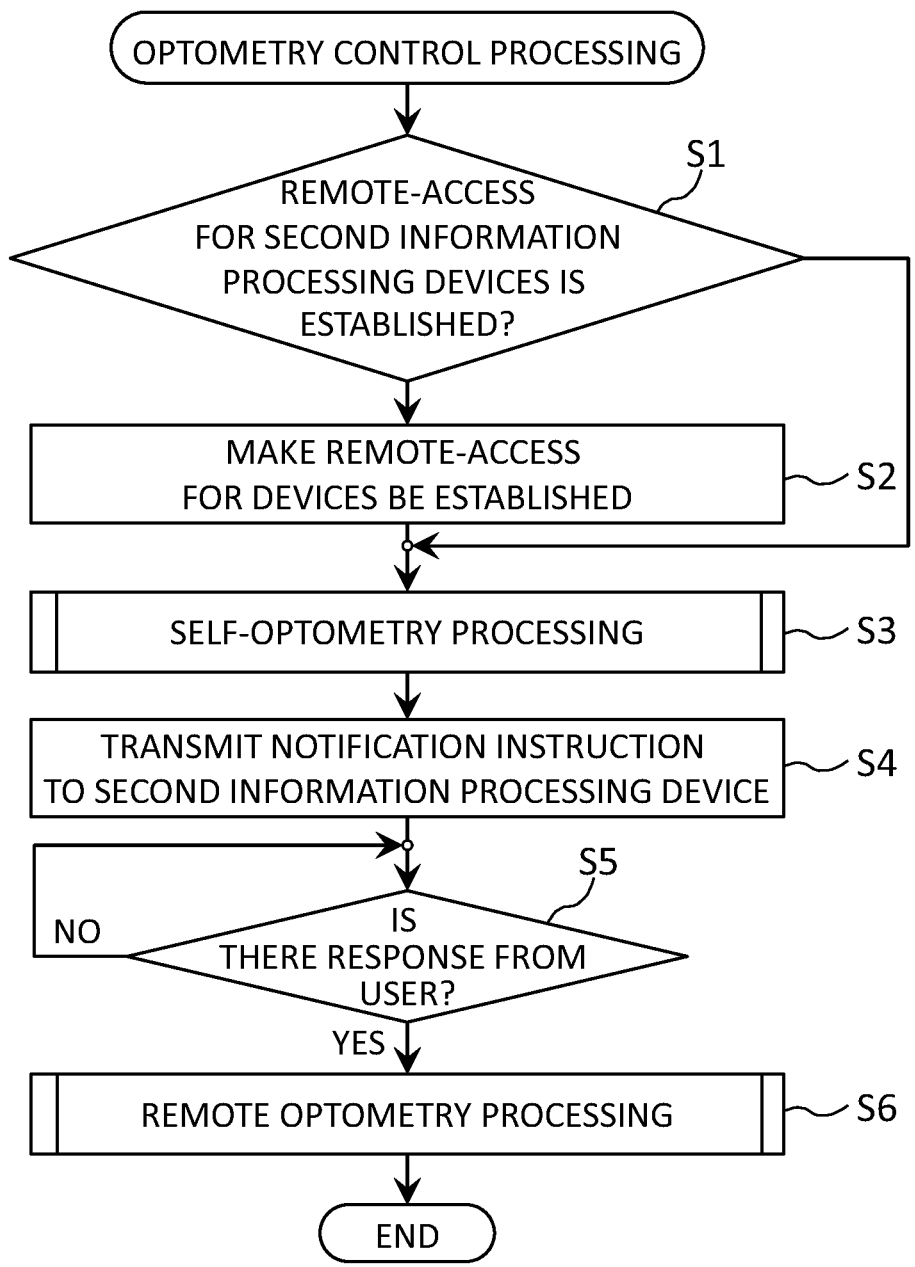
FIG. 2 is a flowchart of optometry control processing performed by a first information processing device 2A.
Figure 4:
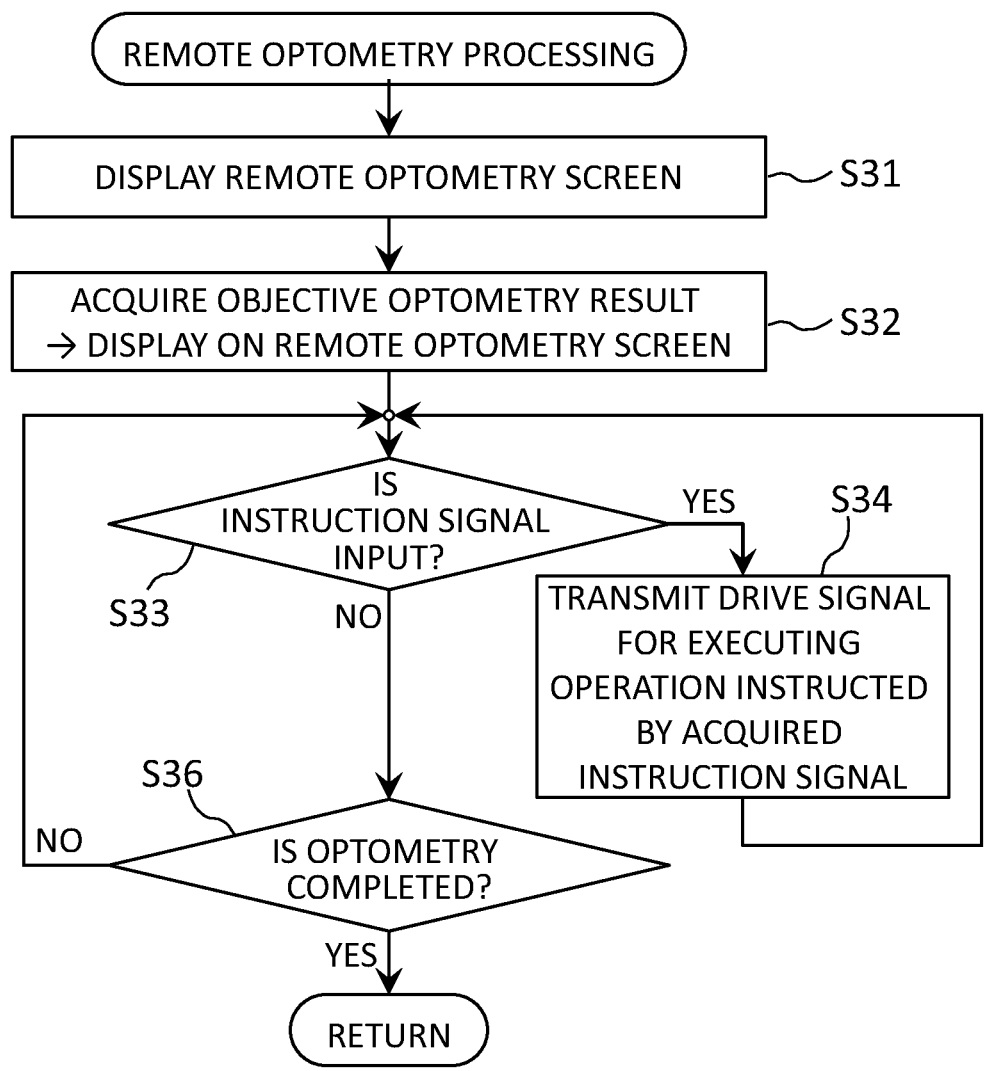
FIG. 4 is a flowchart of remote optometry processing performed during the optometry control processing.

When the processes of S13 to S18 are repeatedly performed and a series of self-optometry is successfully completed (YES in S17), the optometry control processing (refer to FIG. 2) ends as it is without executing the remote optometry processing (refer to S6 in FIG. 2, and FIG. 4).

When the response from the examinee is not input (NO in S15), it is determined whether or not the situation of the self-optometry satisfies a predetermined condition which is likely to be inappropriate (S20). As an example, in the present embodiment, when a predetermined time elapses without a response from the examinee being input after the drive signal is transmitted in S13, it is determined that the predetermined conditions are satisfied. In addition, when the response input by the examinee is inappropriate, it is determined that the predetermined condition are satisfied. When it is determined that the predetermined conditions is satisfied (YES in S20), the process returns to the optometry control processing (refer to FIG. 2), and the optometry method is switched to the remote optometry from self-optometry. At this time, for example, processing for stopping the output of audio, screen, and the like in the self-optometry may be carried out.

In addition, when the response from the examinee is not input (NO in S15) and when the self-optometry condition does not satisfy the condition (NO in S20), the CPU 21A determines whether or not the switching instruction to switch to the remote optometry is input (S21). When it is difficult to perform the self-optometry, the examinee can input a switching instruction to switch to the remote optometry to the operation unit 34A or the first information processing device 2A by voice or the like. When the switching instruction is not input (NO in S21), the process returns to S15, and the processes of S15, S20, and S21 are repeated. When the switching instruction is input (YES in S21), the process returns to the optometry control processing (refer to FIG. 2), and the optometry method is switched to the remote optometry from the self-optometry.

The description will be returned to FIG. 2. When the self-optometry by the self-optometry processing (S3) is not completed, the CPU 21A transmits a notification instruction to one or a plurality of second information processing devices 2B for which the remote-access to the first information processing device 2A is established via the network 5 (S4). The notification instruction is an instruction to perform a notification operation for notifying the user (for example, an examiner, and the like) of the fact that the self-optometry by the first information processing device 2A is completed. The notification operation may be carried out by at least one method such as the audio output and the image display. By executing the notification operation, the user of the second information processing device 2B can more easily grasp the fact that a situation or the like in which the self-optometry cannot be carried out occurs in the first information processing device 2A.

Next, the CPU 21A determines whether or not there is a response from the user (for example, the examiner or the like) of the second information processing device 2B (S5). When there is no response from the examiner of any of the second information processing devices 2B (NO in S5), since it is impossible to perform the remote optometry, the determination in S5 is repeated to enter the standby state. When the user of any second information processing devices 2B is in a state in which the remote optometry can be proceeded, and the response instruction is input to the second information processing device 2B (S5), the CPU 21A performs the remote optometry processing (S6).

The remote optometry processing will be described with reference to FIG. 4. The remote optometry processing is performed by the drive control application. First, the CPU 21A causes the remote optometry screen 50 (refer to FIG. 5) to be displayed on the display unit 35B of the second information processing device 2B used by the examiner who proceeds with the remote optometry (S31).

Figure 5:
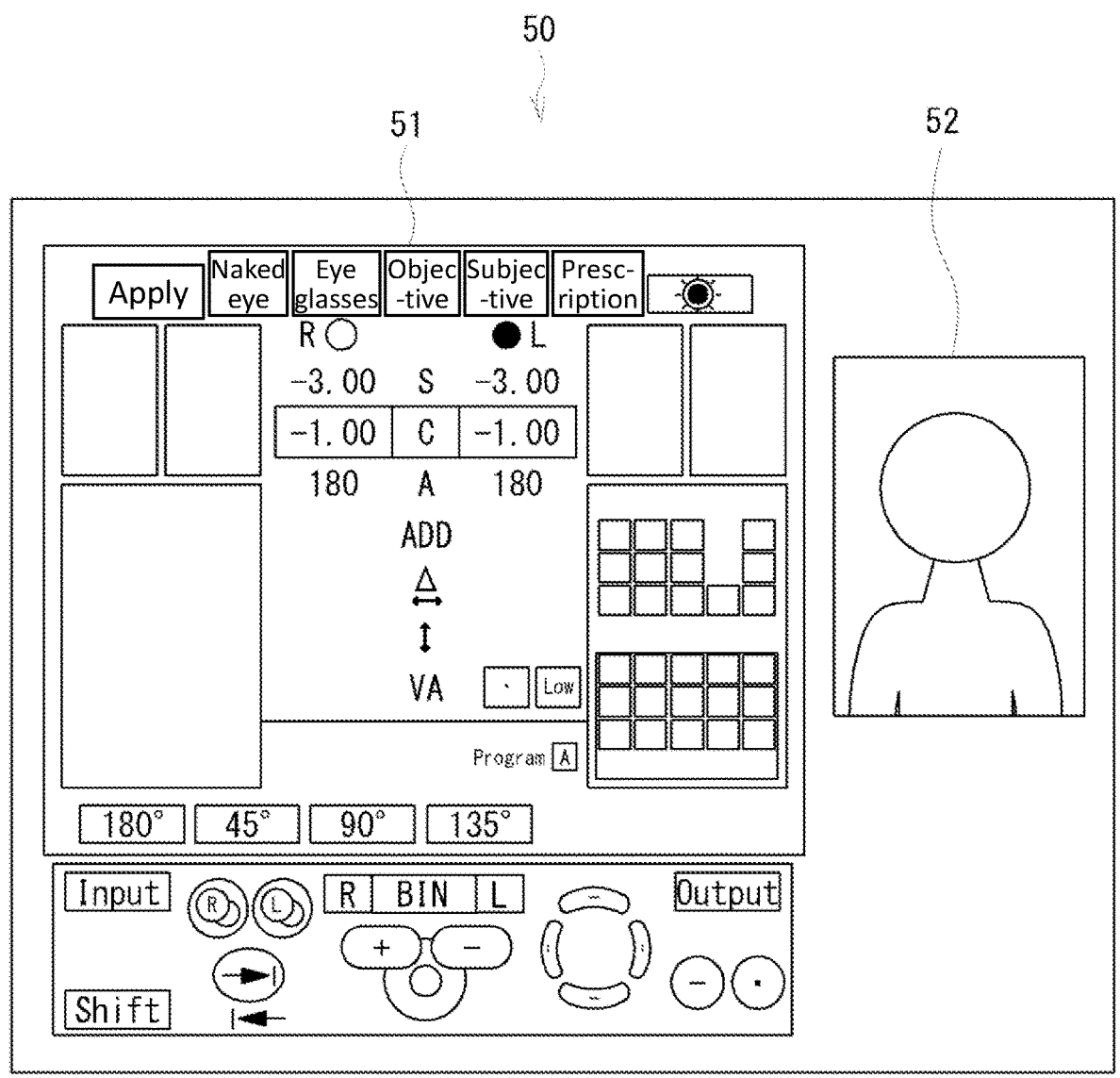
FIG. 5 is a diagram showing an example of a remote optometry screen 50 used in the present embodiment.

As shown in FIG. 5, the remote optometry screen 50 in the present embodiment includes an operation image area 51 and a captured image area 52. The CPU 21A causes an operation image including information on the optical characteristics of the target light flux to be presented to the subject eye to be displayed in the operation image area 51. In the operation image in the present embodiment, the value relating to the optical characteristics of the target light flux presented to the subject eye is displayed for each type of optical characteristics. The examiner can specify a value for a desired type among a plurality of types of optical characteristics (the spherical power, the cylindrical power, the astigmatic axis angle, and the like). In addition, the CPU 21A causes the captured image by the camera 31A connected (or mounted) to the first information processing device 2A to be displayed in the captured image area 52. Therefore, the examiner can check the captured image (for example, the image of the examinee) by the camera 31A together with the operation image during the remote optometry. Therefore, the remote optometry is carried out more smoothly.

In addition, when the objective optometry result for the same examinee is acquired, the CPU 21A displays the acquired result on the remote optometry screen 50 (S32). As described above, the objective examination result may be acquired by various methods.

During the remote optometry, the audio signal input from the microphone 32A to the first information processing device 2A is converted into the voice by the speaker 33B of the second information processing device 2B. In addition, the audio signal input from the microphone 32B to the second information processing device 2B is converted into the voice by the speaker 33A of the first information processing device 2A. Therefore, the examiner and the examinee can have a conversation during the remote optometry. In addition, the image captured by the camera 31B may be displayed on the display unit 35A of the first information processing device 2A.

During the remote optometry, the examiner using the second information processing device 2B can input the instruction signal instructing the operation of the subjective optometry device 1 by at least one of the operation unit 34B and the microphone 32B. The instruction signal is at least one of the instruction signal for arranging the optical element determined by the examiner in the examination window of the calibration optical system 11 and the instruction signals for presenting the target determined by the examiner in the target presentation unit 16.

As an example, in the present embodiment, the examiner can input the instruction signal by operating the mouse as an operation unit 34B. The mouse includes a wheel rotation detection unit, a wheel click detection unit, a left click detection unit, and a right click detection unit. The wheel rotation detection unit detects a rotation direction and an amount of rotation of the wheel rotatably provided on the mouse body. The wheel click detection unit detects a fact that the wheel is clicked (pressed). The left click detection unit detects a fact that a left button provided on the mouse body is clicked (pressed). The right-click detection unit detects a fact that a right button provided on the mouse body is clicked (pressed). The mouse outputs detection signals from each of the wheel rotation detection unit, the wheel click detection unit, the left click detection unit, and the right click detection unit to an information processing device (for example, the second information processing device 2B, or the like).

When a click is detected by at least one of the wheel click detection unit, the left click detection unit, and the right click detection unit, the CPU of the information processing device (in the present embodiment, at least one of the first information processing device 2A and the second information processing device 2B) switches the type (for example, any of the spherical power or the cylindrical power) of the optical characteristics whose value is to be changed, among the optical characteristics of target light flux presented to the subject eye by the subjective optometry device 1. In addition, the CPU of the information processing device changes the value relating to any of a plurality of specific optical types (in the present embodiment, the type specified by clicking) according to the amount and direction of rotation of the wheel detected by the wheel rotation detection unit. Therefore, the examiner can intuitively and smoothly change the value relating to the optical characteristics of the target light flux by rotating the wheel. That is, a case of switching the optical element using a dedicated controller provided with a rotation-operable operation unit and a case of switching the optical element by rotating the wheel are similar to each other in the rotation operation. Therefore, it is possible to intuitively switch the optical element similarly to the case of using a dedicated controller.

When the wheel click is detected by the wheel click detection unit, the CPU may switch the value relating to the optical element. In this case, it may be determined whether the value relating to the optical element is switched to any of "+" and "−" depending on, for example, whether a cursor displayed on the display unit 35A when a click is detected matches the "+" or "−" on the remote optometry screen 50. By using the wheel click, it becomes easy to minutely switch the value relating to the optical element. In addition, the switching of the value relating to the optical element according to the amount and direction of rotation of the wheel and the switching of the value relating to the optical element according to the click of the wheel may be used in combination. In this case, the examiner can appropriately use the intuitive switching of the optical element by rotating the wheel and the minute switching of the optical element by clicking the wheel depending on the situation.

The CPU 21A determines whether or not an instruction signal is input to the second information processing device 2B (S33). When the instruction signal is input to the second information processing device 2B, the input instruction signal is acquired by the first information processing device 2A via the network 5. When the instruction signal is input and acquired (YES in S33), the CPU 21A transmits a drive signal for causing the subjective optometry device 1 to operate as instructed by the acquired instruction signal to the subjective optometry device 1 (S34). As described above, the drive signal is transmitted from the first information processing device 2A to the drivers 12 and 17 via the relay unit 19 (refer to FIG. 1). After that, the process returns to S33. The processes S33 to S36 are repeated until the remote optometry is completed (NO in S36). When the remote optometry completion instruction is input (YES in S36), the optometry control processing ends.

The technologies disclosed in the above embodiment are merely examples. Therefore, the technologies exemplified in the above embodiment can be modified. For example, only some of the technologies exemplified in the above embodiment can also be performed. As an example, the subjective optometry system 100 may perform only one of the self-optometry and the remote optometry. In addition, when both the self-optometry and the remote optometry are carried out, the self-optometry and the remote optometry may be appropriately switched according to the instruction from the user. In this case, the subjective optometry system 100 may set the optometry method to be performed, according to the instruction input by the user among the self-optometry and the remote optometry. The subjective optometry system 100 may start an application for executing the set optometry method at the time of turning on the power or starting the optometry.

Figure 3:
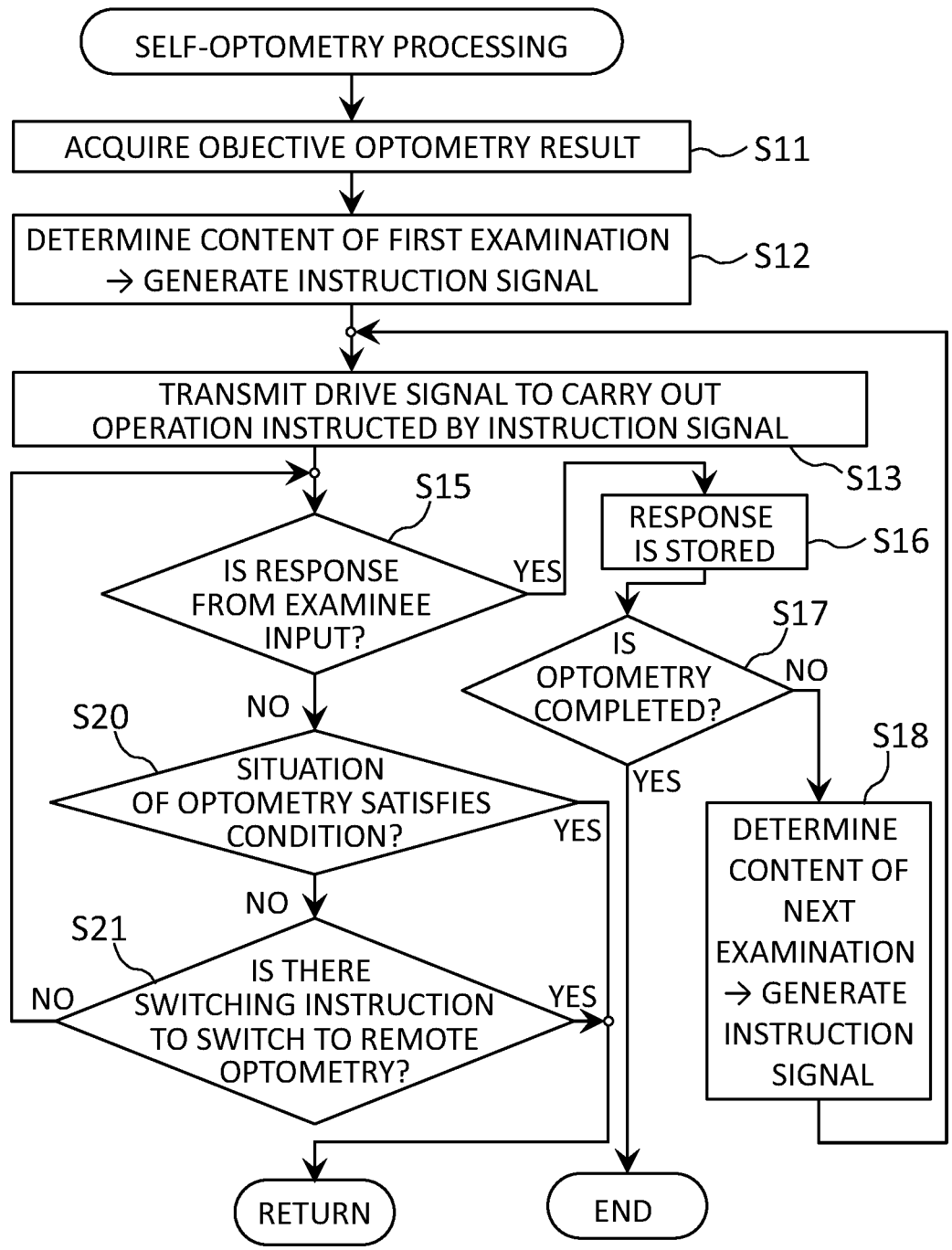
FIG. 3 is a flowchart of self-optometry processing performed during the optometry control processing.

The processing for acquiring the instruction signal in S13 in FIG. 3 and S33 of FIG. 4 is an example of an "instruction signal acquisition step". The processing for transmitting the drive signal in S13 in FIG. 3 and S34 in FIG. 4 is an example of a "drive signal transmission step". The processing for acquiring the response in S15 of FIG. 3 is an example of a "response acquisition step". The processing for generating an instruction signal in S18 in FIG. 3 is an example of an "instruction signal generation step". The processing for switching the optometry method in S20 and S21 in FIG. 3 is an example of an "optometry method switching step". The processing for transmitting the notification instruction in S4 in FIG. 2 is an example of a "notification step".

What is claimed is:

1. A non-transitory computer-readable storage medium storing an optometry control program executed by a first information processing device in a subjective optometry system that includes a subjective optometry device having a calibration optical system that changes optical characteristics of a target light flux presented to a subject eye and is used for subjectively measuring optical characteristics of the subject eye, and the first information processing device connected to the subjective optometry device, the optometry control program comprising:
    a drive control application program for realizing an application that transmits a drive signal for controlling an action of the subjective optometry device to the subjective optometry device; and
    a self-optometry application program for realizing an application that automatically proceeds with an optometry based on a response input by an examinee,
    wherein the drive control application program comprises instructions which, when the drive control application program is executed by a controller of the first information processing device, cause the first information processing device to perform:
        an instruction signal acquisition step of acquiring an instruction signal for instructing an operation of the subjective optometry device; and
        a drive signal transmission step of transmitting the drive signal for causing the subjective optometry device to operate as instructed by the acquired instruction signal to the subjective optometry device,
        wherein in a case where the first information processing device is remote-accessed by a second information processing device which is another information processing device connected via a network, the instruction signal input to the second information processing device by a user is acquired by the first information processing device via the network, in the instruction signal acquisition step,
    wherein the self-optometry application program comprises instructions which, when the self-optometry application program is executed by the controller of the first information processing device, cause the first information processing device to perform:
        a response acquisition step of acquiring a response input by the examinee who visually recognizes a presented target; and
        an instruction signal generation step of generating the instruction signal for instructing an operation of the subjective optometry device based on the acquired response;
    wherein the optometry control program comprises instructions which, when the optometry control program is executed by the controller of the first information processing device, cause the first information processing device to perform an optometry method switching step of switching between a self-optometry which is an optometry carried out by the self-optometry application program, and a remote optometry which is an optometry carried out in response to the instruction signal input to the second information processing device;
    wherein, when an optometry for an examinee is started, the self-optometry is carried out prior to the remote optometry in a state that remote access of one or a plurality of the second information processing devices with respect to the first information processing device is established;
    wherein in the state where the remote access is established, when an instruction signal is input by an examiner to the second information processing device that remote-accesses the first information processing device, the input instruction signal is acquired by the first information processing device,
    wherein in the optometry method switching step to be performed during the self-optometry, the optometry method is switched to the remote optometry by at least one of the second information processing devices for which remote access to the first information processing device is established, in a case where a situation of the self-optometry being carried out satisfies a predetermined condition during the self-optometry or in a case where an instruction to switch to the remote optometry is input during the self-optometry; and wherein the optometry control program comprises instructions which, when the optometry control program is executed by the controller of the first information processing device, cause the first information processing device to perform:

a notification step of causing the second information processing device, for which the remote access to the first information processing device is established, to perform a notification operation to a user, in a case where a situation of the self-optometry being carried out satisfies a predetermined condition or in a case where an instruction to switch to the remote optometry is input.

2. The non-transitory computer-readable storage medium according to claim 1, wherein the optometry control program comprises instructions which, when the optometry control program is executed by the controller of the first information processing device, cause the first information processing device to perform:

a notification step of causing the second information processing device, for which the remote access to the first information processing device is established, to perform a notification operation to a user, in a case where a situation of the self-optometry being carried out satisfies a predetermined condition or in a case where an instruction to switch to the remote optometry is input.

3. A subjective optometry system comprising:

a subjective optometry device having a calibration optical system that changes optical characteristics of a target light flux presented on a subject eye and is used to subjectively measure optical characteristics of the subject eye; and a first information processing device connected to the subjective optometry device, wherein the first information processing device includes a controller to realize:

a drive control application that transmits a drive signal that controls an action of the subjective optometry device to the subjective optometry device; and a self-optometry application that automatically proceeds with an optometry based on a response input by an examinee, wherein the drive control application executes:

an instruction signal acquisition step of acquiring an instruction signal for instructing an operation of the subjective optometry device; and a drive signal transmission step of transmitting the drive signal for causing the subjective optometry device to operate as instructed by the acquired instruction signal to the subjective optometry device, wherein in a case where the first information processing device is remote-accessed by a second information processing device which is another information processing device connected via a network, the instruction signal input to the second information processing device by a user is acquired by the first information processing device via the network, in the instruction signal acquisition step, wherein the self-optometry application executes:

a response acquisition step of acquiring a response input by the examinee who visually recognizes a presented target; and an instruction signal generation step of generating the instruction signal for instructing an operation of the subjective optometry device based on the acquired response;

wherein the subjective optometry system comprises instructions which, when executed by the controller of the first information processing device, cause the first information processing device to perform an optometry method switching step of switching between a self-optometry which is an optometry carried out by the self-optometry application, and a remote optometry which is an optometry carried out in response to the instruction signal input to the second information processing device;

wherein, when an optometry for an examinee is started, the self-optometry is carried out prior to the remote optometry in a state that remote access of one or a plurality of the second information processing devices with respect to the first information processing device is established;

wherein in the state where the remote access is established, when an instruction signal is input by an examiner to the second information processing device that remote-accesses the first information processing device, the input instruction signal is acquired by the first information processing device, wherein in the optometry method switching step to be performed during the self-optometry, the optometry method is switched to the remote optometry by at least one of the second information processing devices for which remote access to the first information processing device is established, in a case where a situation of the self-optometry being carried out satisfies a predetermined condition during the self-optometry or in a case where an instruction to switch to the remote optometry is input during the self-optometry; and wherein the subjective optometry device comprises instructions which, when executed by the controller of the first information processing device, cause the first information processing device to perform:

a notification step of causing the second information processing device, for which the remote access to the first information processing device is established, to perform a notification operation to a user, in a case where a situation of the self-optometry being carried out satisfies a predetermined condition or in a case where an instruction to switch to the remote optometry is input.

* * * * *